United States Patent [19]

Lukacovic et al.

[11] Patent Number: 5,145,666
[45] Date of Patent: Sep. 8, 1992

[54] METHODS OF REDUCING PLAQUE AND GINGIVITIS WITH REDUCED STAINING

[75] Inventors: Michael F. Lukacovic, West Chester; Satyanarayana Majeti, Cincinnati, both of Ohio

[73] Assignee: The Proctor & Gamble Co., Cincinnati, Ohio

[21] Appl. No.: 781,443

[22] Filed: Oct. 23, 1991

[51] Int. Cl.$^5$ .......................... A61K 7/16; A61K 7/18
[52] U.S. Cl. .......................................... 424/52; 424/57
[58] Field of Search ................................... 424/49-58

[56] References Cited

U.S. PATENT DOCUMENTS

| | | | |
|---|---|---|---|
| 2,839,448 | 6/1958 | Hager et al. | 424/49 |
| 2,946,725 | 7/1960 | Norris et al. | 424/52 |
| 3,105,798 | 10/1963 | Holliday et al. | 424/52 |
| 3,282,792 | 11/1966 | Fiscella | 424/52 |
| 3,934,002 | 1/1976 | Haefele | 424/54 |
| 3,957,968 | 5/1976 | Cordon | 424/57 |
| 3,988,433 | 10/1976 | Benedict | 424/53 |
| 4,011,309 | 3/1977 | Lutz | 424/49 |
| 4,256,731 | 3/1981 | Curtis et al. | 424/54 |
| 4,323,551 | 4/1982 | Parran Jr. et al. | 424/54 |
| 4,335,102 | 6/1982 | Nakashima et. al. | 424/52 |
| 4,363,794 | 12/1982 | Ochiai et. al. | 424/52 |
| 4,522,806 | 6/1985 | Muhlemann et al. | 424/52 |
| 4,592,487 | 6/1986 | Simon et. al. | 424/51 |
| 4,670,252 | 6/1987 | Sampathkumar | 424/53 |
| 4,716,035 | 12/1987 | Sampathkumar | 424/52 |
| 4,804,530 | 2/1989 | Sampathkumar | 424/53 |
| 4,822,599 | 4/1989 | Mitra | 424/52 |
| 4,925,655 | 5/1990 | Smigel et al. | 424/52 |
| 4,986,981 | 1/1991 | Glace et al. | 424/50 |
| 4,990,329 | 2/1991 | Sampathkumar | 424/52 |
| 5,004,597 | 4/1991 | Majeti et al. | 424/52 |
| 5,028,414 | 7/1991 | Sampathkumar | 424/52 |
| 5,094,842 | 3/1992 | Riley | 424/52 |
| 5,096,702 | 3/1992 | Rolla et. al. | 424/52 |

FOREIGN PATENT DOCUMENTS

| | | |
|---|---|---|
| 311259 | 4/1989 | European Pat. Off. . |
| 311260 | 4/1989 | European Pat. Off. . |
| 0422803 | 4/1991 | European Pat. Off. . |
| 0427175 | 5/1991 | European Pat. Off. . |

*Primary Examiner*—Shep K. Rose
*Attorney, Agent, or Firm*—D. C. Mohl; J. D. Schaeffer; R. C. Witte

[57] ABSTRACT

Compositions for/methods of reducing plaque and gingivitis with reduced staining.

16 Claims, No Drawings

METHODS OF REDUCING PLAQUE AND GINGIVITIS WITH REDUCED STAINING

TECHNICAL FIELD

The present invention relates to compositions for/-methods of reducing plaque and gingivitis while at the same time not incurring significant staining.

BACKGROUND OF THE INVENTION

Plaque is recognized as a precursor of such oral diseases as caries and gingivitis. The gums of the mouth of humans and lower animals may be harmed by deposits of dental plaque, a combination of minerals and bacteria found in the mouth. The bacteria associated with plaque can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes. This can result in destruction of bone and gum tissue.

With such problems being possible from plaque/gingivitis it is not surprising that extensive efforts have been expended in trying to find effective treatment compositions. Many of these efforts have used quaternary ammonium compounds or bis-biquanides such as chlorhexidine which is used in Peridex® sold by The Procter & Gamble Company.

Another material which has been considered is stannous ion. Such a material is disclosed in Syatun B., "Plaque Inhibiting Effect of Dentifrices Containing Stannous Fluoride", *Acta Odontol. Scand*, 36, 205-210 (1978); and Bay I., and Rolla, G., "Plaque Inhibition and Improved Gingival Condition By Use of a Stannous Fluoride Toothpaste", *Scand. J. Dent. Res.*, 88, 313-315 (1980).

In spite of the many disclosures in the antiplaque/antigingivitis area, the need for improved products still exists. In U.S. Pat. No. 5,004,597, Apr. 2, 1991, to Majeti et al., oral compositions are described containing stannous fluoride stabilized with stannous gluconate. These compositions provide excellent antiplaque and antigingivitis benefits. However the compositions do cause some staining of enamel surfaces.

The present inventors have discovered that the staining can be reduced by the use of a composition containing pyrophosphate ions with the stannous ion formulation.

It is an object of the present invention therefore to provide compositions which deliver an improved antiplaque/antigingivitis benefit with reduced staining.

It is a further object of the present invention to provide improved products utilizing stannous fluoride and stannous gluconate in one composition and pyrophosphate ions in another.

It is still a further object of the present invention to provide an effective method for treating plaque/gingivitis with the above described compositions.

These and other objects will become clearer from the detailed description which follows.

All percentages and ratios used herein are by weight of the total compositions unless otherwise specified. Additionally, all measurements are made at 25° C. in the composition or in an aqueous solution/dispersion unless otherwise specified.

SUMMARY OF THE INVENTION

The present invention embraces oral compositions comprising in one composition:
a) a safe and effective amount of stannous fluoride; and
b) a safe and effective amount of stannous gluconate;
c) a pharmaceutically acceptable carrier
wherein said composition has a pH of from about 3.0 to about 5.0 and is substantially free of calcium ion sources. By "substantially free" is meant less than about 2%; and comprising in a second composition:
a) a safe and effective amount of a pyrophosphate ion source; and
b) a pharmaceutically acceptable carrier.

The present invention also encompasses a method for retarding the development of plaque/gingivitis using these compositions.

DETAILED DESCRIPTION OF THE INVENTION

The stannous compositions of the present invention comprise stannous fluoride and stannous gluconate and a pharmaceutically acceptable carrier. The pyrophosphate compositions comprise pyrophosphate ions and a pharmaceutically acceptable carrier.

By "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carrier", as used herein, is meant a suitable vehicle which is pharmaceutically acceptable and can be used to apply the present compositions in the oral cavity.

Stannous Fluoride

Stannous fluoride is the first essential component of stannous compositions. This material is a staple item of commerce and is present in the stannous composition at a level of from about 0.05% to about 1.1%, preferably from about 0.4% to about 0.95%. It should be recognized that separate soluble stannous and fluoride salts may be used to form stannous fluoride in-situ as well as adding the salt directly. Suitable salts for forming stannous fluoride in-situ include stannous chloride and sodium fluoride among many others.

Stannous Gluconate

Stannous gluconate is the second of the essential components of the present stannous compositions. This material is a known stannous chelate and may be provided to the present compositions as the chelate or as separate soluble stannous and gluconate salts and the chelate formed in-situ such as with stannous fluoride. Such salts include stannous chloride and sodium gluconate. Stannous gluconate is present in the present compositions at a level of from about 0.1% to about 11%, preferably from about 2% to about 4%.

Pharmaceutically Acceptable Carrier

The carrier for the stannous components as well as the pyrophosphate component described herein below can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

The abrasive polishing material contemplated for use in the present invention can be any material which does not excessively abrade enamel and dentin and does not provide calcium ions which may precipitate with, for example, the fluoride ions provided from stannous fluoride. These include, for example, silicas including gels and precipitates, insoluble sodium polymetaphosphate, $\beta$-phase calcium pyrophosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used. Abrasives such as calcium carbonate, calcium phosphate and regular calcium pyrophosphate are not preferred for use in the present compositions since they provide calcium ions which can complex with fluoride ions. However if the calcium ion is controlled such calcium salts may be entirely suitable for use.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the compositions described herein is present at a level of from about 6% to about 70%, preferably from about 15% to about 25% when the dentifrice is a toothpaste. Higher levels, as high as 95%, may be used if the composition is a tooth powder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4.051.234, Sep. 27, 1977, incorporated herein by reference.

It is common to have an additional water-soluble fluoride compound present in dentifrices and other oral compositions in an amount sufficient to give a fluoride ion concentration in the composition at 25° C. and/or when it is used of from about 0.0025% to about 5.0% by weight, preferably from about 0.005% to about 2.0% by weight, to provide additional anticaries effectiveness. Preferred fluorides are sodium fluoride, indium fluoride, and sodium monofluorophosphate in addition to the stannous fluoride. Norris et al., U.S. Pat. No. 2,946,735, issued Jul. 26, 1960 and Widder et al., U.S. Pat. No. 3.678.154, issued Jul. 18, 1972 disclose such salts as well as others. Both patents are incorporated herein by reference.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a total level of from about 15% to about 70%.

Also desirable for inclusion in the toothpastes of the present invention are other stannous salts such as stannous pyrophosphate and antimicrobials such as quaternary ammonium salts, bis-biquanide salts, nonionic antimicrobial salts and flavor oils. Such agents are disclosed in U.S. Pat. No. 2,946,735, Jul. 26, 1960, to Norris et al. and U.S. Pat. No. 4,051,234, Sep. 27, 1977 to Gieske et al., incorporated herein by reference. Noncationic agents are disclosed in U.S. Pat. No. 4,894,220, Jan. 16, 1990, to Nabi et al., incorporated herein by reference. These agents, if present, are included at levels of from about 0.01% to about 1.5%.

Another preferred embodiment of the present invention is a mouthwash composition. Conventional mouthwash composition components can comprise the carrier for the actives of the present invention. Mouthwashes generally comprise from about 20:1 to about 2:1 of a water/ethyl alcohol solution and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 18% to 25%) ethyl alcohol, 0% to 20% (preferably 5% to 20%) of a humectant, 0% to 2% (preferably 0.01% to 0.15%) emulsifying agent, D% to 0.5% (preferably 0.005% to 0.06%) sweetening agent such as saccharin, 0% to 0.3% (preferably 0.03% to 0.3%) flavoring agent, and the balance water. The amount of stannous components in mouthwashes is typically from about 0.01% to about 1.5% by weight.

Suitable lozenge and chewing gum components are disclosed in U.S. Pat. No. 4,083,955, Apr. 11, 1978 to Grabenstetter et al., incorporated herein by reference.

The pH of the present compositions and/or its pH in the mouth can be any pH which is safe for the mouth's hard and soft tissues and will provide optimal effect of the stannous gluconate. Such pH's are from about 3.0 to about 5.0, preferably from about 4.0 to about 5.0, most preferably about 4.5.

Pyrophosphate Compositions

The second composition of the present invention is a composition containing/capable of providing an effective amount of pyrophosphate ions. The pyrophosphate ion found can either be pyrophosphate acid or any of the readily water soluble pyrophosphate salts. Such salts include any of the alkali metal salts such as sodium, potassium and lithium and also including ammonium.

The stannous and pyrophosphate compositions are placed into separate containers if they are liquid or pastes. If a lozenge or a gum, they may not need separate containers but would in most instances be wrapped separately. Irrespective of the product form, they may be packaged as part of a kit.

The amount of pyrophosphate ions is any effective amount generally from about 1% to about 15%, preferably from about 1% to about 10%, most preferably from about 3% to about 7%.

As is indicated above, the pyrophosphate compositions can comprise other components such as those described above for the stannous compositions.

METHOD OF MANUFACTURE

The carrier compositions of the present invention can be made using methods which are common in the oral products area. A specific method of manufacture is set forth in the Examples.

COMPOSITION USE

The present invention in its method aspect involves applying to the oral cavity safe and effective amounts of the compositions described herein. These amounts (e.g. from about 0.3 to about 15g), if it is a toothpaste or mouthwash, are kept in the mouth for from about 15 to about 60 seconds.

The compositions can be used in any order but it is preferable that the stannous composition be used first.

The following examples further describe and demonstrate preferred embodiments within the scope of the present invention. The examples are given solely for illustration and are not to be construed as limitations of this invention as many variations thereof are possible without department from the spirit and scope thereof.

EXAMPLES I-IV

The following dentifrice compositions are representative of the stannous compositions:

| Component | Weight % | | | |
|---|---|---|---|---|
| | I | II | III | IV |
| Water | 12.500 | 12.500 | 12.500 | 12.500 |
| Sorbitol (70% Solution) | 47.891 | 45.727 | 43.437 | 41.328 |
| Glycerin | 10.198 | 10.198 | 10.198 | 10.000 |
| Titanium Dioxide | 0.525 | 0.525 | 0.525 | 0.525 |
| Silica | 20.000 | 20.000 | 20.000 | 20.000 |
| Na Carboxymethyl Cellulose | 1.050 | 1.050 | 1.050 | 1.000 |
| Na Carrageenan | — | — | — | 0.350 |
| Magnesium Alumina Silicate | 0.408 | 0.408 | 0.408 | — |
| Hydroxyethyl Cellulose | — | — | — | — |
| Na Alkyl Sulfate (27.9% Solution) | 4.000 | 4.000 | 4.000 | 4.000 |
| Na Gluconate | 0.632 | 2.395 | 4.790 | 5.514 |
| Stannous Fluoride | 0.454 | 0.454 | 0.454 | 0.454 |
| Stannous Chloride Dihydrate | — | 1.141 | 1.141 | 2.198 |
| Stannous Pyrophosphate | 1.040 | — | — | — |
| Na Saccharin | 0.200 | 0.200 | 0.200 | 0.230 |
| Flavor | 0.851 | 0.851 | 0.851 | 1.000 |
| FD&C Blue #1 (1% Solution) | 0.051 | 0.051 | 0.051 | 0.051 |
| Na Hydroxide (50% Solution) | 0.200 | 0.500 | 0.395 | 0.850 |
| pH | 4.5 | 4.5 | 4.5 | 4.5 |

EXAMPLE IV-VIII

The following are additional stannous dentifrice compositions representative of the present invention:

| Component | Weight % | | | |
|---|---|---|---|---|
| | V | VI | VII | VIII |
| Water | 12.500 | 16.500 | 12.500 | 12.500 |
| Sorbitol (70% Solution) | 45.712 | 42.255 | 45.754 | 45.908 |
| Glycerin | 10.000 | 10.000 | 10.000 | 10.000 |
| PEG-12 | — | 3.000 | — | — |
| Titanium Dioxide | 0.525 | 0.525 | 0.525 | 0.525 |
| Silica | 20.000 | 20.000 | 20.000 | 20.000 |
| Na Carboxymethyl Cellulose | 1.000 | — | 1.000 | 0.900 |
| Na Carrageenan | 0.350 | 0.450 | 0.350 | 0.350 |
| Magnesium Alumina Silicate | — | — | — | — |
| Hydroxyethyl Cellulose | — | 0.400 | — | — |
| Na Alkyl Sulfate (27.9% Solution) | 4.000 | 4.000 | 4.000 | 4.000 |
| Na Gluconate | 2.082 | 2.395 | 2.395 | 2.082 |
| Stannous Fluoride | 0.454 | 0.454 | 0.454 | 0.908 |
| Stannous Chloride Dihydrate | 1.500 | 1.141 | 1.141 | 0.846 |
| Stannous Pyrophosphate | — | — | — | — |
| Na Saccharin | 0.230 | 0.230 | 0.230 | 0.230 |
| Flavor | 1.000 | 1.000 | 1.000 | 1.000 |
| FD&C Blue #1 (1% Solution) | 0.051 | 0.050 | 0.051 | 0.051 |
| Na Hydroxide (50% Solution) | 0.600 | 0.600 | 0.600 | 0.700 |
| pH | 4.5 | 4.5 | 4.5 | 4.5 |

Procedure for Making Dentifrice

In preparing the stannous dentifrice formulations, sorbitol and one half of the water are added to the mix tank and heating to 77° C. initially. Saccharin, titanium dioxide, and silica may be added to the mixture during this heating period. Sufficient agitation is maintained to prevent the settling of the insoluble components. The glycerin is added to a separate vessel and is also heated to 77° C. When both the solutions have attained the required temperature, the carboxymethyl cellulose (CMC) and carrageenan are blended together and slowly added to the glycerin under vigorous agitation. When the CMC and carrageenan are sufficiently dispersed in the glycerin, this mixture is added to the sorbitol/water mixture. The resulting mixture is then blended for a period of time sufficient to allow complete hydration of the binders (about 15 minutes). When the paste is of acceptable texture, the flavor, sodium alkyl sulfate, and color are added. One half of the remaining water is then added to a separate mix tank and allowed to heat to 77° C. After the water attains the necessary temperature, the sodium gluconate is added under medium agitation and allowed to dissolve completely. The stannous chloride dihydrate is then added to the gluconate solution and also allowed to dissolve. This mixture is added to the main mix. The stannous fluoride is added to the remaining water (also at 77° C.) and the resulting solution is added to the main mix and allowed to blend thoroughly before final pH adjustment with sodium hydroxide. The completed paste is agitated for approximately 20 minutes before being milled and deaerated.

EXAMPLE IX

The following is a stannous toothpowder representative of the present invention:

| Component | Weight % |
| --- | --- |
| Stannous Fluoride | 0.454 |
| Stannous Chloride Dihydrate | 1.500 |
| Sodium Gluconate | 2.082 |
| Silica | 74.964 |
| Sodium Sulfate | 20.000 |
| Sodium Lauryl Sulfate | 1.000 |
| Flavor | 1.000 |
| Sodium Saccharin | 0.200 |

EXAMPLE X-XII

The following are stannous topical gels representative of the present invention:

| Component | X | XI | XII |
| --- | --- | --- | --- |
| Stannous Fluoride | 0.454 | 0.454 | 0.454 |
| Stannous Chloride Dihydrate | 1.141 | 1.500 | 2.200 |
| Sodium Gluconate | 1.750 | 2.082 | 2.500 |
| Glycerin | 92.855 | 70.000 | 50.000 |
| Sorbitol (70% Solution) | — | 21.964 | 42.146 |
| Sodium Carboxymethyl Cellulose | 0.600 | 0.800 | — |
| Hydroxyethyl Cellulose | — | — | 0.500 |
| Flavor | 1.000 | 1.000 | 1.000 |
| Sodium Saccharin | 0.200 | 0.200 | 0.200 |
| Sodium Alkyl Sulfate (27.9%) | 2.000 | 2.000 | 1.000 |

EXAMPLE XIII-XVI

The following are stannous mouthrinse tablets representative of the present invention:

| Component | XIII | XIV | XV | XVI |
| --- | --- | --- | --- | --- |
| Stannous Fluoride | 0.100 g | 0.100 g | 0.100 g | 0.100 g |
| Stannous Chloride | 0.375 g | 0.375 g | 0.550 g | 0.375 g |
| Dihydrate | | | | |
| Sodium Gluconate | 0.500 g | 1.000 g | 0.700 g | 0.700 g |
| Flavor | 0.150 g | 0.150 g | 0.150 g | 0.150 g |
| Sodium Saccharin | 0.050 g | 0.050 g | 0.050 g | 0.200 g |
| Mannitol | 1.000 g | — | — | — |
| Sodium Carboxymethyl Cellulose | 0.050 g | — | — | — |
| Gum Arabic | — | — | 2.000 g | — |
| Corn Starch | — | 2.000 g | 0.500 g | — |
| Sodium Benzoate | 0.030 g | 0.030 g | 0.030 g | 0.025 g |
| Citric Acid | — | — | — | 0.200 g |
| Sodium Carbonate | — | — | — | 0.100 g |
| Sodium Bicarbonate | — | — | — | 0.200 g |
| Glycine | — | — | — | 0.050 g |

Given below are pyrophosphate compositions which are representative of the present invention:

EXAMPLE XVII

The following is an example of a pyrophosphate composition useful in the present invention.

| Component | Wt. % |
| --- | --- |
| Sorbitol (70%) | 35.00 |
| Sodium Saccharin | 0.280 |
| FD&C Blue #1 (1.0% Aqueous Solution) | 0.050 |
| Precipitated Silica Abrasive | 24.000 |
| Sodium Fluoride | 0.243 |
| Flavor | 1.044 |
| Sodium Alkyl Sulfate (27.9% Aqueous Solution) | 5.000 |
| Tetrasodium Pyrophosphate | 3.400 |
| Sodium Acid Pyrophosphate | 1.370 |
| Carbomer 940 | 0.250 |
| Xanthan Gum | 0.800 |
| Titanium Dioxide | 0.525 |
| Polyethylene Glycol 300 | 5.000 |
| Water | 23.038 |

What is claimed is:

1. An oral composition effective in treating plaque/gingivitis with reduced staining having a first composition comprising:
   (a) a safe and effective amount of stannous fluoride;
   (b) a safe and effective amount of stannous gluconate; and
   (c) a pharmaceutically acceptable carrier
wherein the pH of said composition is from about 3.0 to about 5.0 and said composition is substantially free of a calcium ion source(s); and a second composition comprising:
   (a) a safe and effective amount of a pyrophosphate ion source;
   (b) a pharmaceutically acceptable carrier.
wherein said compositions are packaged as a kit of separate containers.

2. An oral composition according to claim 1 wherein the amount of stannous fluoride is from about 0.05% to about 1.1%.

3. An oral composition according to claim 2 wherein the amount of stannous gluconate is from about 0.1% to about 11%.

4. An oral composition according to claim 3 wherein the pharmaceutically acceptable carrier for the stannous and pyrophosphate compositions is a toothpaste.

5. An oral composition according to claim 4 wherein the tooth pastes also contain a silica dental abrasive.

6. A stannous oral composition according to claim 5 which also contains another stannous salt.

7. An oral composition according to claim 3 wherein the pharmaceutically acceptable carrier for the stannous and pyrophosphate compositions is a mouthwash.

8. Stannous and pyrophosphate oral compositions according to claim 7 which also contain a material selected from the group consisting of a humectant, ethanol, a nonionic surfactant and mixtures thereof.

9. An oral composition according to claim 3 wherein the pharmaceutically acceptable carrier for the stannous and pyrophosphate compositions is a lozenge.

10. An oral composition according to claim 3 wherein the pharmaceutically acceptable carrier for the stannous and pyrophosphate compositions is a chewing gum.

11. A method of reducing plaque and gingivitis by applying to the oral cavity a safe and effective amount of a stannous composition according to claim followed by a safe and effective amount of the pyrophosphate composition.

12. A method according to claim 11 wherein both the stannous and pyrophosphate compositions are toothpastes.

13. A method according to claim 11 wherein both the stannous and pyrophosphate compositions are mouthwashes.

14. A method according to claim 13 wherein the compositions additionally contain a material selected from the group consisting of a humectant, ethanol, a nonionic surfactant and mixtures thereof.

15. A method according to claim 11 wherein the compositions are a lozenges.

16. A method according to claim 11 wherein the compositions are chewing gums.

* * * * *

UNITED STATES PATENT OFFICE
CERTIFICATE OF CORRECTION

PATENT NO. : 5,145,666
DATED : September 8, 1992
INVENTOR(S) : Michael F. Lukacovic, Satyanarayana Majeti It is certified that error appears in the above-identified patent and that said Letters Patent is hereby corrected as shown below:

Column 1, line 35, "Syatun" should read -- Svatun --.

Column 5, line 6, "D%" should read -- 0% --.

Column 6, line 30, "EXAMPLE IV-VIII" should read -- EXAMPLE V-VIII --.

Column 10, line 1, "claim followed" should read -- claim 1 followed --.

Signed and Sealed this

Fourteenth Day of September, 1993

Attest:

BRUCE LEHMAN

Attesting Officer     Commissioner of Patents and Trademarks